United States Patent [19]

Babic

[11] Patent Number: 4,473,700

[45] Date of Patent: Sep. 25, 1984

[54] 2 OR 3-TETRADECENYL AND POLY ISOBUTENYL SUBSTITUTED N-ALKYL AND N POLYAMINO ALKYLENE PYRROLID-2-ONES

[75] Inventor: Gary T. Babic, Beacon, N.Y.

[73] Assignee: Texaco Inc., White Plains, N.Y.

[21] Appl. No.: 395,362

[22] Filed: Jul. 6, 1982

[51] Int. Cl.³ .......................................... C07D 207/12
[52] U.S. Cl. .................................. 548/543; 549/295; 549/326
[58] Field of Search ................ 549/326, 295; 548/543

[56] References Cited

FOREIGN PATENT DOCUMENTS 144478 1/1962 U.S.S.R. .............................. 549/295

*Primary Examiner*—Paul M. Coughlan, Jr.
*Assistant Examiner*—D. B. Springer
*Attorney, Agent, or Firm*—Robert A. Kulason; James F. Young; James J. O'Loughlin

[57] ABSTRACT

Disclosed are isomeric polyisobutenyl butyrolactones and lactams thereof useful as dispersants in lubricant oils and having the formulas:

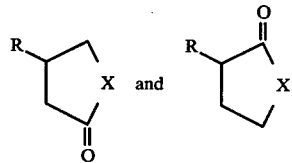

wherein R is a hydrocarbyl group having from 12 to 300 carbon atoms; X is O or >N—R', where R' is an alkyl or alkylamino group having from 1 to 20 carbon atoms and from 0 to 10 nitrogen atoms. The butyrolactones are made by mild reduction of the corresponding cyclic anhydrides and the lactams are prepared by reacting the intermediate butyrolactones with at least a molar equivalent of a primary amine, optionally, in the presence of a base or an acid.

2 Claims, No Drawings

2 OR 3-TETRADECENYL AND POLY ISOBUTENYL SUBSTITUTED N-ALKYL AND N POLYAMINO ALKYLENE PYRROLID-2-ONES

BACKGROUND OF THE INVENTION

1. Field of the Invention

This invention pertains to lubricants having incorporated therein dispersant oil soluble polyisobutenyl butyrolactones and lactams derived therefrom.

Lubricants used in the crankcase of internal combustion engines, gears and power transmitting units become contaminated by foreign particles. Deposition of such particles is known to interfere with proper operation of such mechanisms and accordingly the lubricants must contain dispersant additives which keep the particles highly dispersed in a condition unfavorable for deposition on metals.

2. Discussion of the Prior Art

The relevant prior art includes U.S. Pat. Nos. 3,200,075; 3,272,746; 3,341,542; and 3,775,431.

Of these, the first teaches that certain lactone amides are useful as lubricating oil detergents. U.S. Pat. No. 3,248,187 discloses alkenyl dicarboxylic acid lactones useful as rust inhibitors. U.S. Pat. No. 3,341,542 discloses acylated nitrogenous compounds as dispersing agents in lubricants and which are obtained by condensing a hydroxyalkyl-substituted alkylene amine with an acid. U.S. Pat. No. 3,775,431 reports the synthesis of butyrolactams by reacting a gamma lactone with ammonia or a primary amine over a zeolite.

In the chemical literature, Bloomfield et al, in J. Org. Chem. 32 (12), 3919-24 (1967) disclose the reduction of cyclic anhydrides to lactones or diols with $LiAlH_4$. Bailey et al in J. Org. Chem. 1970, 35 (10), 3574-6 show the reduction of cyclic anhydride with $NaBH_4$. Kayser et al published in Can. J. Chem. 1978, 56 (11), 1524-32 a paper discussing factors affecting the regioselectivity of attack on the carbonyl group of cyclic anhydrides by metal hydrides. To date, however, research on the reduction of compounds having possible utility as lubricant additives has not been extended.

None of the above in any way suggests the present invention.

SUMMARY OF THE INVENTION

In accordance with the product aspect of the invention, there are provided useful compounds of the formulas:

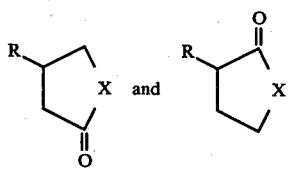

wherein R is a hydrocarbyl group having from 12 to 300 carbon atoms; X is 0 or >N—R' where R' is an alkyl or alkylamino group having 2 to 20 carbon atoms and 0 to 10 nitrogen atoms.

According to the composition aspect of the invention, there are provided lubricants containing a major amount of an oil of lubricating viscosity and a dispersant amount of the above compounds where X is >N—R'.

According to the process aspect of the invention, there is provided a process for preparing polyisobutenylbutyrolactams useful as dispersants in lubricants which comprises reducing a cyclic anhydride to the corresponding lactone in aqueous acid media and condensing the lactone with at least one molar equivalent of a primary amine or polyamine.

DISCLOSURE OF BEST MODE OF PRACTISING THE INVENTION

The starting anhydrides used herein are usually derived from polyolefins, such as polypropylene, polyethylene, polyisobutylene by condensation with maleic anhydride or as disclosed in U.S. Pat. No. 3,272,746, by reaction of a chlorinated polyolefin with maleic anhydride. This patent is incorporated by reference herein.

Reduction of anhydrides to lactones

The reduction of the anhydrides to the corresponding isomeric lactones takes place as shown below:

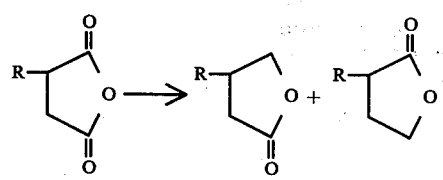

The reaction takes place in an inert solvent with preferably on excess of a mild reducing agent such as $NaBH_4$, $LiAlH_4$, zinc-acetic acid reagent, polymeric amine-borane reducing agents and mixtures thereof. The reaction can proceed with equimolar amounts of the anhydride and of the reducing agent bearing in mind that both $LiAlH_4$ and $NaBH_4$ contain four potential hydrogens so that one mole of anhydride would react with ¼ mole of the reducing agent preferably, by way of successive reductions.

Suitable solvents for the reduction include lower alkanols, preferably isopropanol, toluene, and tetrahydrofuran. The reaction may be carried out by adding all the reducing agent at once or incrementally. The yields are substantially quantitative. To obtain a pure product completely free of diacid, the diacid must be completely dehydrated back to the anhydride. Failure to do so is not critical since the presence of diacid does not interfere with the formation of the final lactams.

The production of lactones from anhydrides was studied using conventional instrumental methods (carbon-13 and proton nuclear magnetic resonance (NMR)), and infrared spectroscopy (IR) and physical methods (elemental analysis and total acid number (TAN) titration). Two preferred exemplary substrates were used in the reaction: tetradecenyl succinic anhydride (TDSA), and a polyisobutenyl succinic anhydride (ASAA) of approximate 1300 molecular weight.

TDSA was utilized in model studies because it was a pure compound and therefore amenable to thorough analysis. $C^{13}$ NMR techniques were used to establish the reaction products from the reduction of TDSA with sodium borohydride as the corresponding butyrolactone. These results are presented in Table 1.

TABLE I $C^{13}$ NMR DATA

| | C=O Chemical Shift, ppm |
|---|---|
| TDSA | 180.76, 178.26 |
| Reduction Product (TD-Lactone) | 180.36, 180.13, 179.26, 178.75 |

TABLE I-continued

| C[13] NMR DATA | |
|---|---|
| TDSA-Diacid | 177.12, 174.82 |

The complete disappearance of the TDSA carbonyl signals following reduction occurs as expected. If some diacid of TDSA is present in the starting material, it is not affected by the reduction and consequently its NMR signals are present before and after the reaction. From a practical standpoint, a small amount of the diacid was convenient as an internal standard for NMR interpretation.

The IR spectra also allowed rapid identification of the reduction product. The characteristic carbonyl absorption for a five-membered anhydride is a pair of sharp peaks centered at approximately 1775 cm$^{-1}$ and 1850 cm$^{-1}$, as reported by R. M. Silverstein and G. C. Bassler, "Spectrometric Identification of Organic Compounds", John Wiley & Sons, New York, N.Y. 1967, p. 75. A five-membered lactone carbonyl absorption is similar, consisting of a sharp peak around 1775 cm$^{-1}$. Howver the peak at 1850 cm$^{-1}$, present for the anhydride, is absent in the lactone. For the particular case of TDSA, the anhydride absorbed at 1777 and 1860 cm$^{-1}$ while the lactones had only a peak at 1780 cm$^{-1}$. Several potential side products were also examined to ascertain that they would not interfere with the IR interpretation. The TDSA diacid had an absorption at 1700 cm$^{-1}$, and a 6-membered lactone, which could be speculated as a rearrangement product, had an absorption at 1740 cm$^{-1}$. Therefore the IR allowed a rapid assessment of the progress of the reaction. For the product of the sodium borohydride reduction of TDSA the sole carbonyl absorption was a sharp peak at 1780 cm$^{-1}$, indicating complete conversion to the butyrolactone.

The TAN is an analytical value derived from the titration of acidic groups. An anhydride should yield two titratable acid groups; a lactone may yield up to one, but the stability of the lactone could reduce this amount. The TAN's for typical TDSA and lactone products are presented in Table 2.

TABLE 2

| | TAN (ASTM D974) | |
|---|---|---|
| Material | found | theory |
| TDSA | 309.5 | 381 |
| TD-Lactone | 167.1 ck | 190.5 max |
| | 177.1 | |

These values confirm the postulated structure of the reaction product.

A variety of reagents were examined for the reduction of TDSA to the butyrolactone. Lithium aluminum hydride and alkoxides can be used but are too expensive for large scale production. Sodium borohydride or zinc dust-acetic acid were found to be two satisfactory reduction systems. Addition of one equivalent of sodium borohydride (four equivalents of hydride) in cold water to one equivalent of TDSA in tetrahydrofuran, stirring at ambient temperature for 1 to 3 hours, followed by acidic workup gives excellent conversion to the TD-butyrolactone. The reaction is vigorous and the sodium borohydride must be added cautiously to moderate the reaction.

The same product was obtained by adding 3 equivalents of zinc dust to a slurry of TDSA in 25% aqueous acetic acid and 3 hours' heating at 60°-100° C. Due to the heterogeneity of the reaction mixture, results were not as consistent with this method as with the use of sodium borohydride. Therefore the translation of the reaction from the TDSA model compound to ASAA was concentrated on the sodium borohydride method, which method is preferred.

The reaction product from the reduction of ASAA with sodium borohydride was also easily characterized by spectroscopy. The results, presented in Table 3, indicate that the butyrolactone is the major product and that no ASAA starting material remains.

TABLE 3

| | IR (cm$^{-1}$) |
|---|---|
| ASAA | 1785, 1860 |
| Reduction Product | 1775 |

Due to the complex nature of the polymeric ASAA, the C$^{13}$ NMR consists of a broad group of signals, which limits its utility. However, the IR absolutely identified the lactone by the peak at 1775 cm$^{-1}$ and the absence of an absorption at 1860 cm$^{-1}$.

The TAN values corroborate this identification. The calculated and theoretical values are presented in Table 4.

TABLE 4

| | TAN (D-974) | |
|---|---|---|
| | found | theory* |
| ASAA | 37.35 | 40 |
| Lactone | 2.29-15.60 | 20 max |

*Adjusted for diluent oil.

Table 5 gives experimental details of the reduction of ASAA to butyrolactones. Successive treatments with sodium borohydride (Example 2) with isopropyl alcohol as solvent gave a very high yield of butyrolactone with no detectable ASAA or diacid present. Because the diacid of ASAA is inert to the sodium borohydride conditions, it is necessary to completely dehydrate the diacid to ASAA between treatments or the diacid will remain in the final product.

In the case of Example 2 this was accomplished by azeotropic distillation with toluene. For all other cases no special dehydration was carried out so the products contained typically 5-15% diacid after sodium borohydride treatment.

Examples 7, 8, and 12 the controls with no reducing agent present to evaluate possible side reactions. In Examples 7 and 12 it is shown that, as might be expected, an alcohol solvent can react with the anhydride to form esters. When alcohol is the only solvent, this esterification is apparently more facile than reduction because even when sodium borohydride or zinc is present (Example 6 and 11) no significant reduction occurs. [Simply heating the anhydride (Example 8) causes no change.] Examples where the reduced product, the butyrolactone, is formed as the major product are Examples 1, 2, 3, 4, 5, 9, 15 and 16.

TABLE 5
Reduction of ASAA to the Corresponding Butyrolactone

| Example | Moles of Reagent per Equivalent of ASAA[1] | Solvent | Temperature | Time | Workup | TAN (D974) | IR SPECTRUM |
|---|---|---|---|---|---|---|---|
| 1 | 4 NaBH$_4$ | isoOH[a] | ambient | 12 hr | strip | 11.90 | lactone + diacid |
| 2[b] | 3 × 4 NaBH$_4$ | isoOH/tol | ambient | 12 hr | strip | 2.29 | lactone |
| 3 | 4 NaBH$_4$ | isoOH | 5° C. | 0.5 hr | strip | 11.40 | lactone + diacid |
| 4 | 4 NaBH$_4$ | THF | ambient | 1 hr | strip | 12.68 | lactone + diacid |
| 5 | 4 NaBH$_4$ | THF | ambient | 12 hr | strip | 10.60 | lactone + diacid |
| 6 | 4 NaBH$_4$ | isoOH | 50° C. | 1 hr | strip | 22.09 | ester + diacid |
| 7 | None | isoOH | 50° C. | 1 hr | strip | 21.40 | ester + diacid |
| 8 | None | None | 50° C. | 1 hour | None | 37.35 | anhydride |
| 9 | 4 Zn dust | 25% HOAc | ambient | 1.5 hr | strip | 14.98 | lactone + 20% S.M. |
| 10 | 4 Zn dust | 25% HOAc | 60° C. | 1 hr | strip | 17.66 | 90% S.M.[d] |
| 11 | 4 Zn dust | EtOH | 60° C. | 1 hr | strip | 13.95 | ester |
| 12 | None | EtOH | 60° C. | 1 hr | strip | 13.80 | ester |
| 13 | 4 Zn dust | 3N HCl | 60° C. | 1 hr | strip | 22.40 | diacid + S.M. |
| 14 | 4 Zn dust | 25% HOAc | 80° C. | 2 hr | strip | 14.60 | diacid + S.M. |
| 15 | 4 Amborane TM 355[c] | heptane | ambient | 4 hr | strip | 15.60 | lactone + S.M. |
| 16 | 8 Ambrone TM 355[c] | heptane | ambient | 4 hr | strip | 12.81 | lactone + S.M. |

[a]Isopropanol.
[b]Three (3) sequential reactions, azeotroping off H$_2$O between reactions.
[c]Polymeric amine-borane reducing agent.
[d]Starting material.

Lactam formation

The inventive lactams are formed by condensing the above-prepared lactone intermediates with at least one mole of a primary amine in an inert solvent such as toluene or a light mineral oil as follows:

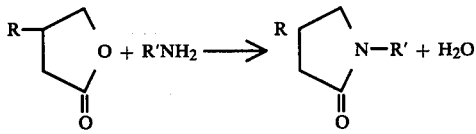

where R and R' are as above

Any R'NH$_2$ compound containing a primary amine group in its structure is amenable to this reaction. Typical amines include, but are not limited to, diethylenetetramine, triethylene-tetraamine, tetraethylenepentaamine, and bis-aminopropyl ethylenediamine. Results with EDA indicate that the reaction may be acid or base-catalyzed. This data is presented in Table 6. EDA was convenient for the study of this reaction because any excess reagent could be readily removed and the nitrogen content of the lactam would indicate the completeness of the reaction.

A preferred reaction sequence for the conversion of lactone to lactam is as follows: 100 grams (0.05 mole) of derived lactone is added to a stirred mixture of 102 g of 100E Pale Stock HF and 9.0 g (0.15 mole) of ethylenediamine. Catalyst, if any, is added. The reaction mixture is heated to 160° for 2 hours under a nitrogen purge in a round-bottom flask fitted with a stirrer and a Dean-Stark for removal of any overhead. After 2 hours the mixture is filtered, stripped under aspirator vacuum at 90° C. for one hour to remove excess amine, and refiltered.

For the higher boiling amines only one equivalent of amine is used in the reaction. Any solid catalyst is removed in the filtration. The overhead in the reaction consists of some amine, water (either as a byproduct of the reaction or from the catalyst system) and a small amount of low-boiling hydrocarbons from the 100E Pale Stock HF.

TABLE 6

| Catalyst | % N |
|---|---|
| None | 0.28, 0.30 |
| HCL | 0.24 |
| glacial HOAc | 0.38–0.53 |
| p-toluenesulfonic acid | 0.33 |
| NaOH | 0.42 |
| Theory | 0.55 |

The reaction can also be followed by IR as the carbonyl absorption of the lactone (at 1775 cm$^{-1}$) disappears and an absorption characteristic of a 5-membered lactam appears (at 1720 cm$^{-1}$).

To this effect, the lactams prepared as above-described were evaluated for their dispersant properties with the Bench VC Test. The test involves degrading lubricating oils with artificially generated blow-by and measuring the turbidity of the resulting blend. The test correlates well with sludge values in the Sequence V-D test.

In order to demonstrate the utility of lactams as dispersants it was necessary to establish the absence of any succinimide which may result from residual ASAA or diacid in the lactone. These succinimides are known to be excellent dispersants. Therefore a batch of lactone essentially free of unreacted ASAA or diacid was prepared by sequential reduction with sodium borohydride. By IR analysis (lack of absorption at 1860 cm$^{-1}$) there is found less than 5% ASAA present and therefore after treatment with EDA less than 5% succinimide would be formed. The dispersancy of this lactam product in diluent oil, containing less than 5% succinimide was greater than that of the succinimide in the same oil. The difference in performance is therefore attributable to the lactam present. Results are presented in Table 7.

TABLE 7

| Additive | Bench VC Results[1] | |
|---|---|---|
| | 2% | 3% |
| Lactam containing maximum of 5% EDA succinimide | 66.5 | 54.0 |
| Butyrolactone prior to EDA treatment | 99.0 | 98.0 |
| 5% EDA succinimide in diluent oil | 81.0 | 73.0 |
| 100% EDA succinimide | 54.5 | 49.5 |

TABLE 7-continued

| Additive | Bench VC Results[1] | |
|---|---|---|
|  | 2% | 3% |
| Typical EDA Lactams | | |
| 1. from NaBH₄ Lactones: | 55.5 | 50.5 |
| 2. from Zn/HOAc Lactones: | 57.5 | 52.5 |

[1] Dispersancy test - lower numbers indicate better dispersancy. Additive blended in a typical 10W-30 lubricating oil blend without supplemental dispersants.

Results from the above bench VC Test indicate that the EDA lactams prepared from ASAA-derived lactones are approximately equivalent in dispersancy to EDA succinimides prepared from the ASAA. It should be noted that succinimides are currently in wide commercial use as lubricating oil additives.

A fully formulated lubricating oil in accordance with this invention contains a major amount of an oil of lubricating viscosity from 0.5 to 10 percent by weight of the inventive lactams as well as conventional lube oil additives such as VI improvers, corrosion inhibitors, detergents, dispersants in an amount sufficient to fulfill each additive's function therein.

While there have been described herein what are at present considered preferred embodiments of the invention, it will be obvious to those skilled in the art that minor modifications and changes may be made without departing from the essence of the invention. It is therefore to be understood that the exemplary embodiments are illustrative and not restrictive to the invention, the scope of which is defined in the appended claims and that all modification that come within the meaning and ranges of equivalency of the claims are intended to be included therein.

What is claimed is:

1. A compound of the formula:

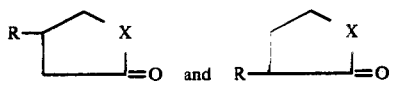

in which R is a monovalent hydrocarbyl radical selected from the class consisting of tetradecenyl and polyisobutenyl in which the polyisobutenyl derivative has an approximate molecular weight of 1300, and X is the divalent N—R' radical where R' is an alkyl or alkylamino group having from 2 to 20 carbon atoms and from 0 to 10 amino groups.

2. The compound of claim 1, wherein X is an N—R' substituent derived from diethylenetetramine, triethylenetetramine, tetraethylenepentamine or bis-aminopropyl ethylenediamine.

* * * * *